(12) United States Patent
Wu

(10) Patent No.: US 6,890,756 B2
(45) Date of Patent: May 10, 2005

(54) METHOD OF USING CYANIDE-FREE LYSE SOLUTION TO EMULATE A CYANIDE-CONTAINING LYSE SOLUTION IN THE MEASUREMENT OF HEMOGLOBIN

(75) Inventor: Jiong Wu, La Vista, NE (US)

(73) Assignee: Streck Laboratories, Inc., La Vista, NE (US)

( * ) Notice: Subject to any disclaimer, the term of this patent is extended or adjusted under 35 U.S.C. 154(b) by 163 days.

(21) Appl. No.: 10/408,827

(22) Filed: Apr. 7, 2003

(65) Prior Publication Data

US 2004/0048386 A1 Mar. 11, 2004

Related U.S. Application Data

(60) Provisional application No. 60/370,537, filed on Apr. 5, 2002.

(51) Int. Cl.$^7$ .............................................. G01N 33/72
(52) U.S. Cl. ......................... 436/66; 436/63; 436/164; 436/166; 436/175; 436/15; 435/2
(58) Field of Search ........................... 436/63, 66, 164, 436/166, 174, 175, 15; 435/2

(56) References Cited

U.S. PATENT DOCUMENTS

| | | | |
|---|---|---|---|
| 4,853,338 A | 8/1989 | Benezra et al. | 436/66 |
| 5,242,832 A | 9/1993 | Sakata | 436/17 |
| 5,250,437 A * | 10/1993 | Toda et al. | 436/10 |
| 5,468,640 A | 11/1995 | Benezra et al. | 436/66 |
| 5,612,223 A | 3/1997 | Kim et al. | 436/17 |
| 5,763,280 A | 6/1998 | Li et al. | 436/66 |
| 5,834,315 A | 11/1998 | Riesgo et al. | 436/66 |
| 5,866,428 A | 2/1999 | Kim et al. | 436/66 |
| 5,882,934 A | 3/1999 | Li et al. | 436/66 |
| 5,958,781 A | 9/1999 | Wong et al. | 436/63 |
| 6,740,527 B1 * | 5/2004 | Wong et al. | 436/17 |
| 2002/0173043 A1 * | 11/2002 | Merabet et al. | 436/66 |
| 2003/0044995 A1 * | 3/2003 | Merabet et al. | 436/66 |

OTHER PUBLICATIONS

Russell, C.D.; Pauling, L., "The Magnetic Properties of the Compounds Ethylisocyanide–Ferrohemoglobin and Imidazole–Ferrihemoglobin," *Proceedings of the National Academy of Sciences*, vol. 25 (1939), pp. 517–522.

Keilin, D.; Hartree, E.F., "Purification of Horse–Radish Peroxidase and Comparison of its Properties with those of Catalase and Methaemoglobin," *The Biochemical Journal*, vol. 49 (1951), pp. 88–104.

Scheler, W.; Schoffa, G.; and Jung, F., "Lichtabsorption und Paramagnetische Suszeptibilitätbei Derivaten des Pferde– und Chironomus–Methämoglobins sowie des Pferde–Metmyoglobins", *Biochemische Zeitschrift*, Band 329 (1957), pp. 232–246.

Diven, W.F.; Goldsack, D.E., Alberty, R.A., "Temperature Jump Kinetic Studies of the Binding of Imidazole by Sperm Whale Metmyoglobin", *The Journal of Biological Chemistry*, vol. 240, No. 6 (Jun., 1965), pp. 2437–2441.

Oshiro, I.; Takenaka, T.; Maeda, J., "New Method for Hemoglobin Determination by Using Sodium Lauryl Sulfate (SLS)." *Clinical Biochemistry*, vol. 15, No. 2 (Apr., 1982), pp. 83–88.

Antonini, E. and Brunori, M., "Specific Aspects of the Reactions of Hemoglobin with Ligands." In: Neuberger, A. and Tatum, E.L., *Frontiers of Biology vol. 21: Hemoglobin and Myoglobin In Their Reactions with Ligands* (Amsterdam, North–Holland Publishing Company, 1971), pp. 235–285.

* cited by examiner

Primary Examiner—Maureen M. Wallenhorst
(74) Attorney, Agent, or Firm—Howrey Simon Arnold & White LLP

(57) ABSTRACT

A method of emulating with a cyanide-free lyse solution, the measurement of hemoglobin in whole blood using a cyanide-containing lyse solution. Such an illustrative method includes: a) combining a predetermined amount of the whole blood sample with a predetermined amount of a cyanide-free lyse solution to form a mixture, b) developing the mixture to a molar absorbtivity ($\epsilon$) in the range of about 12.4 to 12.6 mM$^{-1}$cm$^{-1}$, and c) measuring a level of light absorbance of the mixture at a wavelength of about 540 nm. In one preferred illustrative embodiment, the cyanide-free lyse solution includes: a quaternary ammonium salt surfactant, an anionic surfactant, a hemoglobin binding agent selected from the group consisting of imidazole or hydroxylamine, and an aqueous medium. In one preferred embodiment, the molar absorbtivity is developed to a value of about 12.5 mM$^{-1}$cm$^{-1}$. That is to say to a level that is substantially identical to that of the prior art standard, cyanomethemoglobin. By achieving this level of molar absorbtivity, the final calculated results do not have to be corrected for the different molar absorbtivity exhibited by imidazolemethemoglobin or hydroxylaminemethemoglobin.

16 Claims, No Drawings

METHOD OF USING CYANIDE-FREE LYSE SOLUTION TO EMULATE A CYANIDE-CONTAINING LYSE SOLUTION IN THE MEASUREMENT OF HEMOGLOBIN

Priority is claimed to U.S. provisional patent application No. 60/370,537, filed Apr. 5, 2002, the contents of which is incorporated herein by reference.

BACKGROUND

Hemoglobin, a respiratory heme protein, is commonly present in the blood of vertebrates. Elemental oxygen molecules bind to the iron atoms of the hemoglobin in the lungs where oxygen is abundant, and are released later in tissues that need oxygen. Depending on the oxidation states of heme iron, two forms of hemoglobin, ferrous hemoglobin ($Fe^{2+}$) and ferric (or met) hemoglobin ($Fe^{3+}$) are found naturally. Both forms of protein can bind with various ligands in solution. A characteristic visible spectrum is generally associated with each species of liganded hemoglobin.

The determination of total hemoglobin is indicative of the oxygen-carrying capacity of whole blood. An ability to measure hemoglobin (Hgb) in blood samples is an essential part of diagnostic analysis and is also important for monitoring responsiveness to therapies directed towards diseases which affect hemoglobin and to therapies which are directed towards other diseases but which may have adverse side effects on the hemoglobin level.

Leukocytes in the peripheral blood of normal subjects consist of five types, i.e., lymphocytes, monocytes, neutrophils, cosinophils and basophils. The latter three types of leukocytes are collectively referred to as granulocytes. Different types of leukocytes have different biological functionalities. Counting and differentiating different types of leukocytes in a blood sample provides valuable information for clinical diagnosis.

The counting and classification of leukocytes has most commonly been conducted by automatic hematology analyzers. They employ a hemoloytic reagent to lyse erythrocytes and produce a sample only containing leukocytes. The sample mixture then is analyzed by impedance method. It is important that the lyse reagent not damage the leukocytes. A more sophisticated apparatus has been developed that counts different types of leukocytes (differential counting) including lymphoid (lymphocyte) and myeloid (monocyte and granulocyte) populations. Ideally, one would like to be able to accomplish multiple diagnostic analyses such as hemoglobin measurement and counting the number of leukocytes or differential counting of leukocyte subpopulations in a single automated step.

Hemoglobin count, in g/dL, can be accurately obtained using automated hematology analyzers. Most analyzers use potassium cyanide (KCN) as the key component in lysing agent, due to the extremely stable absorption peak at 540 nm for cyanomethemoglobin. A single-wavelength light absorption measurement is designed for these instruments, in order to give the absorbance (A540) of cyanomethemoglobin solution, and subsequently, the correct count of hemoglobin (HGB) in whole blood or control samples.

The cyanide hemoglobin method has been recommended as a standard by the International Committee for Standardization in Hematology. Modification of this method has led to its wide usage in clinical laboratories. In this method, the iron ion of heme group in all forms of hemoglobin of the red cells are oxidized to methemoglobin by potassium ferricyanide. The methemoglobin is then complexed with cyanide anion, which has a very high affinity to iron ion of the heme group, to form a cyanmethemoglobin chromogen. This extremely stable chromogen has a maximum absorption at 540 nm, which is measured manually by UV spectrometry.

Despite the stable chromogens formed by the standard cyanmethemoglobin method and its modified automatic methods, It is important to develop a cyanide free reagent because the potassium cyanide reagent has caused raised environmental concern with waste disposal. In last ten years, a effort has been given to develop automated hemoglobin analysis methods without utilizing cyanide.

SUMMARY OF THE ILLUSTRATIVE EMBODIMENTS

The present invention is generally directed to a method of determining the hemoglobin content of a whole blood sample using a cyanide-free lyse solution. The illustrative method includes: combining a predetermined amount of the whole blood sample with a predetermined amount of a cyanide-free lyse solution to form a mixture, developing the mixture to a molar absorbtivity (ε) in the range of about 12.4 to 12.6 $mM^{-1}cm^{-1}$, measuring a level of light absorbance of the mixture at a wavelength of about 540 nm, and calculating the hemoglobin content of the whole blood sample. The cyanide-free lyse solution includes: a quaternary ammonium salt surfactant, an anionic surfactant, a hemoglobin binding agent selected from the group consisting of imidazole or hydroxylamine, and an aqueous medium. In one preferred embodiment, the molar absorbtivity is developed to a value of about 12.5 $mM^{-1}cm^{-1}$, that is to say to a level that is substantially identical to that of the prior art standard, cyanomethemoglobin. By achieving this level of molar absorbtivity, the final calculated results do not have to be corrected for the different molar absorbtivity exhibited by imidazolemethemoglobin or hydroxylaminemethemoglobin. A mixture of surfactants is used as part of the lyse solution to effectively lyse the red blood cells without damage to the white blood cells. A quaternary ammonium salt surfactant and an anionic surfactant combination are utilized and in one preferred illustrative embodiment the quaternary ammonium salt is a $C_1$ to $C_{20}$ trimethylammonium salt and the anionic surfactant is preferably sodium lauryl sulfate. The lyse solution is aqueous based and preferably the aqueous medium is selected from water, saline solution, and buffered saline solution and other similar suitable aqueous solutions that should be known to one of skill in the art. Other properties of the aqueous solution include that the pH should be in compatible range, preferably the cyanide-free lyse solution has a pH value from about 3 to less than 12 and more preferably a pH value from about 8 to about 10. The aqueous solution may be hypotonic, isotonic or hypertonic, but preferably the cyanide-free lyse solution has an osmolality from about 20 to about 800/mOsm.

Another illustrative embodiment includes a method of emulating with a cyanide-free lyse solution, the measurement of hemoglobin in whole blood using a cyanide-containing lyse solution. Such an illustrative method includes: a) combining a predetermined amount of the whole blood sample with a predetermined amount of a cyanide-free lyse solution to form a mixture, b) developing the mixture to a molar absorbtivity (ε) in the range of about 12.4 to 12.6 $mM^{-1}cm^{-1}$, and c) measuring a level of light absorbance of the mixture at a wavelength of about 540 nm. In one preferred illustrative embodiment, the cyanide-free lyse solution includes: a quaternary ammonium salt surfactant, an anionic surfactant, a hemoglobin binding agent selected from the group consisting of imidazole or hydroxylamine, and an aqueous medium. In one preferred embodiment, the molar absorbtivity is developed to a value of about 12.5 $mM^{-1}cm^{-1}$. That is to say the molar absorbtivity level that is substantially identical to that of the prior art standard, cyanomethemoglobin. By achieving this level of molar absorbtivity, the final calculated results do not have to be corrected for the different molar absorbtivity exhibited by imidazolemethemoglobin or hydroxylaminemethemoglobin. A mixture of surfactants is used as part of the lyse solution to effectively lyse the red blood cells without damage to the white blood cells. A quaternary ammonium salt surfactant and an anionic surfactant combination are utilized and in one preferred illustrative embodiment the quaternary ammonium salt is a $C_1$ to $C_{20}$ trimethylammonium salt and the anionic surfactant is preferably sodium lauryl sulfate. The lyse solution is aqueous based and preferably the aqueous medium is selected from water, saline solution, and buffered saline solution and other similar suitable aqueous solutions that should be known to one of skill in the art. Other properties of the aqueous solution include that the pH should be in compatible range, preferably the cyanide-free lyse solution has a pH value from about 3 to less than 12 and more preferably a pH value from about 8 to about 10. The aqueous solution may be hypotonic, isotonic or hypertonic, but preferably the cyanide-free lyse solution has an osmolality from about 20 to about 800 mOsm.

The present invention will be more fully understood and appreciated by one of ordinary skill in the art upon review of the following.

DESCRIPTION OF ILLUSTRATIVE EMBODIMENTS

A suitable lyse solution for use in the methods of the present invention should meet certain requirements, such as good precision, good accuracy (vs. the current Lyse), low cost, and stable long-term performance. Additional requirements, such as high within-run precision, good accuracy of other parameters, good linearity and long-term stability are also desirable. These results are achieved by the cyanide-free lyse solutions utilized in the methods of the present invention.

As previously noted above, most hematology analyzers use potassium cyanide (KCN) as the key component in lysing agent for complexing hemoglobin because of the extremely stable absorption peak at 540 nm for cyanomethemoglobin. A single-wavelength light absorption measurement is designed for these instruments, in order to give the absorbance or transmittance of cyanomethemoglobin solution. The correct count of hemoglobin (HGB or Hb) in whole blood or control samples can be obtained using the formula:

$$HGB = \frac{(64000 \text{ g/mol})}{(10 \text{ dL/L})} \times \frac{A_{540}}{\varepsilon_{540} l}$$

or $$HGB = \frac{(64000 \text{ g/mol})}{(10 \text{ dL/L})} \times \frac{-\log(T_{540})}{\varepsilon_{540} l}$$

where $A_{540}$ and $T_{540}$ are absorbance and transmittance of cyanomethemoglobin solution at 540 nm, respectively, $\varepsilon_{540}$ is the molar absorption coefficient (in $mM^{-1}cm^{-1}$) of $Hb^+CN^-$ (12.5 $mM^{-1}cm^{-1}$), l is the pathlength of light (in cm), 64000 g/mol is the molecular weight for human hemoglobin, and HGB is the hemoglobin count in g/dL.

In the formulation of a cyanide-free lysing agent, the fundamental key is to find a hemoglobin binding ligand that can provide a similar absorption at 540 nm:

$$\varepsilon(Hb^+CN^-) \times c \times 1 = [P \times \varepsilon(Hb^+X) + (1-P) \times \varepsilon(Hb^+)] \times c \times 1$$

where X is the new ligand for the reaction $Hb^+ + X \rightleftharpoons Hb^+X$, P is the percent of ligand-bound methemoglobin, $Hb^+X$, at the time of absorption measurement occurs (after a few seconds of mixing), and (1–P) is the percent of free (unbound) methemoglobin, $Hb^+$ at that time. P can be any number between 0 and 1, depending on the binding property of ligand X. For cyanide, the value of P should be very close to 1, due to the extremely fast and tight binding between methemoglobin and $CN^-$. When imidazole is used in the lyse solution of the present invention, a mixture containing approximately 70% $Hb^+$-imidazole and approximately 30% free methemoglobin is generated at the preferred time of measurement (i.e. 25 seconds). Such a hemoglobin mixture gives a nearly identical absorbance to that of HbCN at 540 nm. That is to say the mixture of imidazole-methemoglobin/hemoglobin/unbound imidazole produce a fluid that has an molar absorbtivity that is nearly identical to HbCN. Alternatively hydroxylamine can be utilized to achieve substantially the same result as imidazole.

In one illustrative embodiment of the present invention, the cyanide-free lyse solution utilized contains about 100 to about 500 parts by weight of a quaternary ammonium salt, such as a $C_1$–$C_{20}$ trimethylammonium salt. The role of the quaternary ammonium salts is to substantially lyse the red blood cells and thus should be present in sufficient concentrations to do so without disturbing the white blood cells. In one illustrative and preferred embodiment, the quaternary ammonium salt is a dodecyltrimethyl ammonium salt or tetradecyltrimethyl ammonium salt. The counter ion should be suitable to ionically balance the salt with out adversely affecting the functioning of the lyse solution. Thus in or illustrative embodiment, a halogen anion, and more preferably chloride ion is selected.

The cyanide-free lyse solution utilized in the method of the present illustrative embodiment also includes about 1 to about 5 parts by weight of an anionic surfactant, preferably one based on an alkyl sulfate. The anionic surfactant, in combination with the quaternary ammonium salt, serves to substantially lyse the red blood cells, thus releasing the hemoglobin into solution. In one particularly preferred illustrative embodiment, a lauryl sulfate serves as the alkyl sulfate. To balance the ionic charge, a suitable cation is selected that does not substantially interfere with the functioning of the solution. Thus alkali metal ions are preferred and sodium ion is especially preferred.

As required by hematology analyzers, the combination of quaternary ammonium ion and alkyl sulfate ion essentially lyse the red blood cells completely, following the addition of lysing solution to diluted blood samples, while giving no additional impact to white blood cells (WBC) and platelets (PLT).

The cyanide-free lyse solution utilized in the method of the present illustrative embodiment also includes 50 to about 400 parts by weight of a hemoglobin complexing agent such as imidazole or hydroxylamine. Imidazole, an organic compound containing a five-member ring with two nitrogens and three carbons, is small enough to penetrate into heme pocket to bind with ferric iron, due to the electrostatic attraction between the positive charge on the heme $Fe^{3+}$ and the partial negative charge on the nitrogen of imidazole. The binding of imidazole as a ligand to hemoglobin has been well studied. An absorption peak at 534 nm is observed for the imidazole-bound methemoglobin, which makes imidazole a suitable replacement for cyanide to give an accurate HGB count in hematology analysis. Similarly, the binding of hydroxylamine to the hemoglobin gives a suitable absorption peak for the hydroxylamine-bound methemoglobin, which makes hydroxylamine a suitable replacement for cyanide to give an accurate HGB count in hematology analysis.

An aqueous solution of the above compounds is formulated and utilized as the cyanide-free lyse solution of the present invention. The aqueous solution utilized as the base solution for the cyanide-free lyse solution of the present invention may be water, saline solution, buffered saline solution, or other similar suitable aqueous solutions that should be known to one of skill in the art. The illustrative cyanide-free lyse solution preferably has a pH value from about 3 to less than 12 and more preferably a pH value from about 8 to about 10. To avoid damage to the white blood cells, the illustrative cyanide-free lyse solution is formulated so as to have an osmolality from about 20 to about 800 mOsm.

While not intending to be bound to any particular theory or mechanism of operation, it is believed that a balance of reaction kinetics and molar absorbtivity of the ligand bound methemoglobin are significant factors in the success of the present invention. As noted above, the reaction of the free ligand with the methemoglobin in solution to form a ligand bound methemoglobin can be generally represented by the simplified formula:

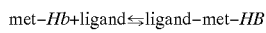

The kinetic rate of reaction at which the ligand binds to the methemoglobin depends upon many factors including the temperature (which for all practical purposes is room temperature), the concentration of the methemoglobin and the concentration of the ligand. One of skill in the art will appreciate that given a known concentration of ligand, a predetermined amount of time for the mixture to reach a point of completion can be related to the concentration of methemoglobin. If the reaction mixture is passed through a flow through absorption cell, the absorbance level of the solution will increase when longer time periods from mixing are used. That is to say, the absorbance increases as the time from mixing to the time of measurement of absorbance increases. One of skill in the art should appreciate that the increase in absorbance over time is related to the concentration of the methemoglobin. For the reaction of cyanide ion with methemoglobin this reaction is very rapid (i.e. within a few seconds) and thus full development of the final absorbance value is achieved soon after mixing of the lyse solution and the whole blood. For other ligands the reaction will be slower (i.e. within several minutes) and thus only partial development of the final absorbance value is achieved by the time the absorbance spectrum is measured by the automated hematology instruments. One of skill in the art should also appreciate that the binding of different ligands to the methemoglobin will also result in chemical species that have molar absorbtivity values different (either greater or smaller) from that of cyanomethemoglobin. Further one of skill in the art should appreciate that there generally is a fixed amount of time between the mixing of the lyse solution and whole blood in a hematology analyzer and the time absorbance of the solution (and thus the concentration of hemoglobin) is measured. This time period is typically 20–30 seconds and more typically 25 seconds. As noted above, for the reaction of cyanide ion with methemoglobin 20–30 seconds is much longer than is required to obtain completion of the reaction, i.e. full development of the absorbance. However, for other ligands this time period is not sufficient to achieve completion of the reaction and thus full development of the absorbance. With the above knowledge, one of skill in the art should appreciate that one can find a point in time at which the absorbance of the solution containing a known amount of hemoglobin and excess ligand approximates that of cyanohemoglobin at the same concentration hemoglobin. Thus by careful selection of the ligand, the ligand concentration in relation to the methemoglobin, the mixing ratio and dilution ratio, it is thus possible emulate the absorbance of a cyanomethemoglobin solution using a solution containing ligands other than cyanide. During the course of such trials, it has been discovered that imidazole and hydroxylamine have the balance of reaction kinetics, molar absorbtivity and stability of the final complex formed, that are suitable to achieve this result. By achieving this result, one of skill in the art should appreciate that by practicing the methods of the present invention, recalibration of a hematology analyzer is not necessary when changing from a cyanide-based lyse solution to a cyanide-free solution used in accordance with the methods of the present invention.

The following examples are included to demonstrate preferred embodiments of the invention. It should be appreciated by those of skill in the art that the techniques and compositions disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLE 1

The following illustrative formulations including dodecyltrimethylammounium chloride (C12), sodium lauryl sulfate (SDS) and imidazole in aqueous solution were utilized to analyze the hemoglobin content of samples in accordance with the methods of the present invention. An Abbott CELL-DYN™ 3500 or 3700 was utilized in making the measurements on whole blood samples. The following table presents representative results in which:

Reference: CD3500 HGB Lyse
Formula 1: 0.315% SDS+0.90% NaCl
Formula 2: 3.225% C12+0.0315% SDS+2.25% Imidazole
Formula 3: 3.225% C12+0.0315% SDS+2.80% Imidazole (pH adjusted to 8.1)
Formula 4: 3.225% C12+0.0315% SDS+4.00% Imidazole (pH adjusted to 8.9)

Para 12 (P12) is a whole blood hematology control commercially available from Streck Laboratories Inc. La Vista, Nebr., USA.

|  | Reference | Formula 1 | Dev. (1) | Formula 2 | Dev. (2) | Formula 3 | Dev. (3) |
|---|---|---|---|---|---|---|---|
| HGB (g/dL) | | | | | | | |
| WB (JW) | 15.83 | 14.75 | −1.08 | 15.20 | −0.63 | 15.20 | −0.63 |
| WB (GK) | 17.20 | 16.20 | −1.00 | 16.65 | −0.55 | 16.70 | −0.50 |
| WB (JE) | 15.33 | 14.30 | −1.03 | 14.60 | −0.73 | 14.70 | −0.63 |
| P12+ Low | 8.14 | 7.18 | −0.96 | 7.73 | −0.41 | 7.74 | −0.40 |
| P12+ Normal | 13.30 | 12.10 | −1.20 | 12.50 | −0.80 | 12.70 | −0.60 |
| P12+ High | 16.90 | 15.80 | −1.10 | 16.30 | −0.60 | 16.30 | −0.60 |
| WBC (K/µL) | | | | | | | |
| WB (JW) | 7.77 | 7.73 | −0.04 | 7.80 | 0.03 | 7.86 | 0.09 |
| WB (GK) | 5.46 | 5.46 | 0.00 | 5.62 | 0.16 | 5.71 | 0.25 |
| WB (JE) | 4.19 | 4.17 | −0.02 | 4.10 | −0.09 | 4.21 | 0.02 |
| P12+ Low | 2.96 | 3.04 | 0.08 | 3.07 | 0.11 | 2.92 | −0.04 |
| P12+ Normal | 7.96 | 7.98 | 0.02 | 7.98 | 0.02 | 7.89 | −0.07 |
| P12+ High | 19.20 | 19.10 | −0.10 | 19.20 | 0.00 | 19.60 | 0.40 |

|  | Reference | Formula 4 | Dev. (4) |
|---|---|---|---|
| HGB (g/dL) | | | |
| WB (TL) | 14.80 | 14.35 | −0.45 |
| WB (DS) | 15.70 | 15.15 | −0.55 |
| WB (GH) | 15.55 | 15.15 | −0.40 |
| WBC (K/µL) | | | |
| WB (TL) | 6.59 | 6.66 | 0.07 |
| WB (DS) | 4.45 | 4.48 | 0.03 |
| WB (GH) | 7.00 | 6.92 | −0.08 |

Upon review of the above representative data one of skill in the art should note that the hemoglobin (HGB) count was too low (by about 1 unit), using SDS alone in solution but that the SDS did not affect the WBC count.

It should also be appreciated that the HGB counts were lowered by 0.4–0.8 unit from the reference, using imidazole at high concentrations (2.25%, 2.80% and 4.00%) and that a very slight improvement in HGB was observed as the concentration of imidazole increases. This is believed to be the result of the shorter reaction time allowed by CD 3500 and thus the reaction mixture contains more free methemoglobin and less imidazole-bound hemoglobin at the time of measurement occurs. Consequently, the corresponding absorbance at 540 nm and the HGB count are lower than the reference while the WBC count was not affected.

EXAMPLE 2

The following illustrative formulations including dodecyltrimethylammounium chloride (C12), sodium lauryl sulfate (SDS) and hydroxylamine in aqueous solution were utilized to analyze the hemoglobin content of samples in accordance with the methods of the present invention. An Abbott CELL-DYN™ 3500 was utilized in making the measurements on whole blood samples. The following table presents representative results in which Reference: CD3500 HGB Lyse Formula 5: 3.225% C12+0.0315% SDS+1.00% NH$_2$OH—HCl Formula 6: 3.225% C12+0.0315% SDS+0.50% NH$_2$OH—HCl Formula 7: 3.225% C12+0.0315% SDS+0.10% NH$_2$OH—HCl Para 12 (P12) is a whole blood hematology control commercially available from Streck Laboratories Inc. La Vista, Nebr., USA.

|  | Reference | Formula 5 | Dev. (5) | Formula 6 | Dev. (6) | Formula 7 | Dev. (7) |
|---|---|---|---|---|---|---|---|
| HGB (g/dL) | | | | | | | |
| WB (TL) | 14.80 | 15.97 | 1.17 | 15.73 | 0.93 | 14.20 | −0.60 |
| WB (DS) | 15.70 | 17 | 1.30 | 16.7 | 1.00 | 15.20 | −0.50 |
| WB (GH) | 15.55 | 16.8 | 1.25 | 16.5 | 0.95 | 14.90 | −0.65 |
| WBC (K/µL) | | | | | | | |
| WB (TL) | 6.59 | 6.61 | 0.02 | 6.71 | 0.12 | 6.51 | −0.08 |

-continued

|  | Reference | Formula 5 | Dev. (5) | Formula 6 | Dev. (6) | Formula 7 | Dev. (7) |
|---|---|---|---|---|---|---|---|
| WB (DS) | 4.45 | 4.54 | 0.09 | 4.51 | 0.06 | 4.53 | 0.08 |
| WB (GH) | 7.00 | 7.04 | 0.04 | 7.09 | 0.09 | 7.28 | 0.28 |

Upon review of the above results, one of skill in the art should appreciate that the HGB counts revealed by formulas 5, 6 and 7 show that hydroxylamine is a suitable ligand for practicing the methods of the present invention. It should also be noted that the concentrations of 1% (Formula 5) and 0.5% (Formula 6) appear to be too high, resulting in higher HGB counts than the reference values. In contrast, the concentration of 0.1% hydroxylamine (Formula 7) appears to be too low. Thus the ideal concentration of $NH_2OH$—HCl seems to be between 0.1% and 0.5%, if other components of the lyse remain the same.

Hydroxylamine was also tested as a possible ligand in the cyanide-free lyse study for a different instrument, specifically an Excell 22. Because it made some shift in the white blood cell histogram and thus using hydroxylamine may not be suitable for all applications. It was also noted that the WIC plots from Formulas 5, 6 and 7 did not match with the reference well. This is believed to be due to the lysing agents using Formulas 5, 6 and 7 not being as strong as the reference lyse.

EXAMPLE 3

The following illustrative formulations including tetradecyltrimethylammounium chloride (C14), sodium lauryl sulfate (SDS) and hydroxylamine in aqueous solution were utilized to analyze the hemoglobin content of samples in accordance with the methods of the present invention. An Abbott CELL-DYN™ 3500 was utilized in making the measurements on whole blood samples. The following table presents representative results in which
Reference: CD3500 HGB Lyse
Formula 8: 3.00% C14+0.20% $NH_2OH$—HCl
Formula 9: 3.00% C14+0.10% $NH_2OH$—HCl
Formula 10: 3.00% C14+0.08% $NH_2OH$—HCl, pH 4.5

Para 12 (P12) is a whole blood hematology control commercially available from Streck Laboratories Inc. La Vista, Nebr., USA.

Upon review of the above results, one of skill in the art should appreciate that formula 10, containing 3% C14 and 0.08% hydroxylamine, provided good precision (data not shown) and accuracy in hemoglobin and white blood cell counts. The deviation in hemoglobin was within ±/−0.3 unit, consistent with the requirement by most of the hematology instruments.

It should also be appreciated that the 3% C14 is a much stronger lyse than (3.225% C12+0.0315% SDS) and thus it makes the hemoglobin to be released to solution in a shorter time, and allows longer reaction time for hemoglobin-ligand binding. For example, a 0.1% hydroxylamine in the C14 lyse (Formula 9) gave higher hemoglobin counts by 0.2–0.5 units which is in contrast with a 0.1% hydroxylamine in the C12 lyse (Formula 7) gave lower hemoglobin count by 0.5–0.7 unit. The white blood cell plots using Formulas 8, 9 and 10 were very much improved, consistent with the reference.

EXAMPLE 4

The following illustrative formulations including dodecyltrimethylammounium chloride (C12), sodium lauryl sulfate (SDS) and imidazole in aqueous solution were utilized to analyze the hemoglobin content of samples in accordance with the methods of the present invention. An ADVIA 70 (Excell 22) automated hematology analyzer was utilized in making the measurements on whole blood samples. The following table presents representative results in which:

The reference lyse solution was the commercially available ADVIA 70 Lyse (with cyanide).

The cyanide-free lyse had a formulation of: 3.225% by weight C12; 0.0315% by weight SDS; 2.25% by weight imidzole, and exhibited a pH=9.2±0.3, and Osmolality= 360±10 mOsm.

Para 12 (P12) is a whole blood hematology control commercially available from Streck Laboratories Inc. La Vista, Nebr., USA.

|  | Reference | Formula 8 | Dev. (8) | Formula 9 | Dev. (9) | Formula 10 | Dev. (10) |
|---|---|---|---|---|---|---|---|
| HGB (g/dL) | | | | | | | |
| WB (TL) | 14.93 | 15.65 | 0.72 | 15.1 | 0.17 | 14.80 | −0.13 |
| WB (DS) | 15.70 | 16.5 | 0.80 | 16.05 | 0.35 | 15.60 | −0.10 |
| WB (GH) | 15.58 | 16.45 | 0.87 | 16.05 | 0.47 | 15.58 | 0.00 |
| P12+ Low | 7.95 | | | | | 8.13 | 0.18 |
| P12+ Normal | 13.05 | | | | | 12.95 | −0.10 |
| P12+ High | 17.65 | | | | | 17.35 | −0.30 |
| WBC (K/µL) | | | | | | | |
| WB (TL) | 6.38 | 6.35 | −0.03 | 6.67 | 0.29 | 6.40 | 0.02 |
| WB (DS) | 4.45 | 4.48 | 0.03 | 4.62 | 0.17 | 4.48 | 0.03 |
| WB (GH) | 6.93 | 6.93 | 0.00 | 7.17 | 0.24 | 7.03 | 0.10 |
| P12+ Low | 3.09 | | | | | 2.84 | −0.25 |
| P12+ Normal | 8.27 | | | | | 8.13 | −0.14 |
| P12+ High | 19.40 | | | | | 19.40 | 0.00 |

|  | HGB (g/dL) | | | WBC (K/μL) | | |
|---|---|---|---|---|---|---|
|  | Reference | CN-free | Deviation | Reference | CN-free | Deviation |
| WB (ER) | 13.35 | 13.38 | 0.03 | 8.13 | 8.30 | 0.17 |
| WB (SS) | 14.00 | 13.85 | −0.15 | 6.08 | 6.18 | 0.10 |
| WB (LH) | 14.33 | 14.53 | 0.20 | 6.67 | 6.75 | 0.08 |
| WB (BR) | 16.47 | 16.47 | 0.00 | 6.73 | 6.80 | 0.07 |
| WB (DS) | 15.27 | 15.28 | 0.01 | 5.43 | 5.53 | 0.10 |
| WB (CH) | 12.60 | 12.58 | −0.02 | 6.73 | 6.96 | 0.23 |
| WB (JW) | 16.10 | 16.00 | −0.10 | 8.27 | 8.38 | 0.11 |
| WB (TL) | 15.20 | 15.17 | −0.03 | 6.60 | 6.67 | 0.07 |
| P12+ LOW | 8.33 | 8.46 | 0.13 | 2.83 | 2.88 | 0.05 |
| P12+ NORMAL | 13.37 | 13.42 | 0.05 | 7.70 | 7.74 | 0.04 |
| P12+ HIGH | 18.73 | 18.54 | −0.19 | 18.03 | 18.18 | 0.15 |

Upon review of the above results, one of skill in the art should appreciate that the above cyanide-free lyse containing dodecyltrimethylammounium chloride; sodium lauryl sulfate and imidazole provided good precision and accuracy in hemoglobin and white blood cell counts. The deviation in hemoglobin was consistent with the requirement by most of the hematology instruments. It should also be appreciated that by varying the amount of imidazole or hydroxylamine in the lyse solution, the method of the present invention can be practiced with a variety of automated hematology analyzers. Finally, it should be appreciated by one of skill in the art that recalibration when changing from a cyanide-containing lyse solution to a cyanide-free lyse solution is not necessary.

In view of the above disclosure, one of ordinary skill in the art should understand and appreciate that one illustrative embodiment of the present invention includes a method of determining the hemoglobin content of a whole blood sample using a cyanide-free lyse solution. The illustrative method includes: combining a predetermined amount of the whole blood sample with a predetermined amount of a cyanide-free lyse solution to form a mixture, developing the mixture to a molar absorbtivity (ϵ) in the range of about 12.4 to 12.6 $mM^{-1}cm^{-1}$, measuring a level of light absorbance of the mixture at a wavelength of about 540 nm, and calculating the hemoglobin content of the whole blood sample. The cyanide-free lyse solution includes: a quaternary ammonium salt surfactant, an anionic surfactant, a hemoglobin binding agent selected from the group consisting of imidazole or hydroxylamine, and an aqueous medium. In one preferred embodiment, the molar absorbtivity is developed to a value of about 12.5 $mM^{-1}cm^{-1}$.that is to say to a level that is substantially identical to that of the prior art standard, cyanomethemoglobin. By achieving this level of molar absorbtivity, the final calculated results do not have to be corrected for the different molar absorbtivity exhibited by imidazolemethemoglobin or hydroxylaminemethemoglobin. A mixture of surfactants is used as part of the lyse solution to effectively lyse the red blood cells without damage to the white blood cells. A quaternary ammonium salt surfactant and an anionic surfactant combination are utilized and in one preferred illustrative embodiment the quaternary ammonium salt is a $C_1$ to $C_{20}$ trimethylammonium salt and the anionic surfactant is preferably sodium lauryl sulfate. The lyse solution is aqueous based and preferably the aqueous medium is selected from water, saline solution, and buffered saline solution and other similar suitable aqueous solutions that should be known to one of skill in the art. Other properties of the aqueous solution include that the pH should be in compatible range, preferably the cyanide-free lyse solution has a pH value from about 3 to less than 12 and more preferably a pH value from about 8 to about 10. The aqueous solution may be hypotonic, isotonic or hypertonic, but preferably the cyanide-free lyse solution has an osmolality from about 20 to about 800 mOsm.

Another illustrative embodiment includes a method of emulating with a cyanidefree lyse solution, the measurement of hemoglobin in whole blood using a cyanidecontaining lyse solution. Such an illustrative method includes: a) combining a predetermined amount of the whole blood sample with a predetermined amount of a cyanide-free lyse solution to form a mixture, b) developing the mixture to a molar absorbtivity (ϵ) in the range of about 12.4 to 12.6 $mM^{-1}cm^{-1}$, and c) measuring a level of light absorbance of the mixture at a wavelength of about 540 nm. In one preferred illustrative embodiment, the cyanide-free lyse solution includes: a quaternary ammonium salt surfactant, an anionic surfactant, a hemoglobin binding agent selected from the group consisting of imidazole or hydroxylamine, and an aqueous medium. In one preferred embodiment, the molar absorbtivity is developed to a value of about 12.5 $mM^{-1}cm^{-1}$.that is to say to a level that is substantially identical to that of the prior art standard, cyanomethemoglobin. By achieving this level of molar absorbtivity, the final calculated results do not have to be corrected for the different molar absorbtivity exhibited by imidazolemethemoglobin or hydroxylaminemethemoglobin. A mixture of surfactants is used as part of the lyse solution to effectively lyse the red blood cells without damage to the white blood cells. A quaternary ammonium salt surfactant and an anionic surfactant combination are utilized and in one preferred illustrative embodiment the quaternary ammonium salt is a $C_1$ to $C_{20}$ trimethylammonium salt and the anionic surfactant is preferably sodium lauryl sulfate. The lyse solution is aqueous based and preferably the aqueous medium is selected from water, saline solution, and buffered saline solution and other similar suitable aqueous solutions that should be known to one of skill in the art. Other properties of the aqueous solution include that the pH should be in compatible range, preferably the cyanide-free lyse solution has a pH value from about 3 to less than 12 and more preferably a pH value from about 8 to about 10. The aqueous solution may be hypotonic, isotonic or hypertonic, but preferably the cyanide-free lyse solution has an osmolality from about 20 to about 800 mOsm.

While the apparatus, compositions and methods of this invention have been described in terms of preferred or illustrative embodiments, it will be apparent to those of skill in the art that variations may be applied to the process described herein without departing from the concept and scope of the invention. All such similar substitutes and modifications apparent to those skilled in the art are deemed to be within the scope and concept of the invention as it is set out in the following claims.

What is claimed is:

1. A method of determining the hemoglobin content of a whole blood sample, the method comprising:
    a) combining a predetermined amount of the whole blood sample with a predetermined amount of a cyanide-free lyse solution to form a mixture, wherein the cyanide-free lyse solution includes: a quaternary ammonium salt surfactant, an anionic surfactant, a hemoglobin binding agent selected from the group consisting of imidazole and hydroxylamine, and an aqueous medium;
    b) developing the mixture to a molar absorbtivity ($\epsilon$) in the range of about 12.4 to 12.6 $mM^{-1}cm^{-1}$,
    c) measuring a level of light absorbance of the mixture at a wavelength of about 540 nm, and
    d) calculating the hemoglobin content of the whole blood sample.

2. The method of claim 1, wherein the molar absorbtivity is developed to a value of about 12.5 $mM^{-1}cm^{-1}$.

3. The method of claim 1, wherein the quaternary ammonium salt surfactant is a $C_1$ to $C_{20}$ trimethylammonium salt.

4. The method of claim 1, wherein the anionic surfactant is sodium lauryl sulfate.

5. The method of claim 1, wherein the aqueous medium is selected from the group consisting of water, saline solution, and buffered saline solution.

6. The method of claim 1, wherein the cyanide-free lyse solution has a pH value from about 3 to less than 12.

7. The method of claim 1, wherein the cyanide-free lyse solution has a pH value from about 8 to about 10.

8. The method of claim 1, wherein the cyanide-free lyse solution has an osmolality from about 20 to about 800 mOsm.

9. A method of emulating with a cyanide-free lyse solution, the measurement of hemoglobin in whole blood using a cyanide-containing lyse solution, the method comprising:
    a) combining a predetermined amount of a whole blood sample with a predetermined amount of a cyanide-free lyse solution to form a mixture, wherein the cyanide-free lyse solution includes: a quaternary ammonium salt surfactant, an anionic surfactant, a hemoglobin binding agent selected from the group consisting of imidazole and hydroxylamine, and an aqueous medium;
    b) developing the mixture to a molar absorbtivity ($\epsilon$) in the range of about 12.4 to 12.6 $mM^{-1}cm^{-1}$, and
    c) measuring a level of light absorbance of the mixture at a wavelength of about 540 nm.

10. The method of claim 9, wherein the molar absorbtivity is developed to a value of about 12.5 $mM^{-1}cm^{-1}$.

11. The method of claim 9, wherein the quaternary ammonium salt surfactant is a $C_1$ to $C_{20}$ trimethylammonium salt.

12. The method of claim 9, wherein the anionic surfactant is sodium lauryl sulfate.

13. The method of claim 9, wherein the aqueous medium is selected from the group consisting of water, saline solution, and buffered saline solution.

14. The method of claim 9, wherein the cyanide-free lyse solution has a pH value from about 3 to about 12.

15. The method of claim 9, wherein the cyanide-free lyse solution has a pH value from about 8 to about 10.

16. The method of claim 9, wherein the cyanide-free lyse solution has an osmolality from about 20 to about 800 mOsm.

* * * * *